US00PP09771P

United States Patent [19]

Cunningham

[11] Patent Number: Plant 9,771

[45] Date of Patent: Dec. 31, 1996

[54] ROBINIA PLANT NAMED 'LACE LADY'

[75] Inventor: Peter Cunningham, Auckland, New Zealand

[73] Assignees: Trustees of the Peter Cunningham Family Trust; Trustees of the Sharyn Cunningham Family Trust, both of Auckland, New Zealand

[21] Appl. No.: 428,703

[22] Filed: Apr. 25, 1995

[51] Int. Cl.[6] ..... A01H 5/00

[52] U.S. Cl. ..... Plt./51.1

[58] Field of Search ..... Plt./51.1, 52

*Primary Examiner*—James R. Feyrer

*Attorney, Agent, or Firm*—Burns, Doane, Swecker & Mathis, L.L.P.

[57] ABSTRACT

A distinctive new variety of *Robinia pseudoacacia* having a a bushy shrub growth habit is provided. The branches have a generally short zigzag internodal growth configuration. Miniature spines commonly are present on at least some of the branches. The mature leaves commonly possess severely curled leaflets.

2 Drawing Sheets

SUMMARY OF THE INVENTION

The new variety of *Robinia pseudoacacia* was discovered during 1985 as a chance seedling among plants of the same species growing in a cultivated area at Kumeu, near Auckland, New Zealand. I was attracted to a single plant that exhibited a highly uncharacteristic shrub growth habit unlike that of other plants of the species growing nearby. Because of its unique growth habit and overall appearance the plant of the new variety was carefully preserved and was evaluated.

The new *Robinia pseudoacacia* variety of the invention was found to exhibit:

(a) a bushy shrub growth habit;
(b) the formation of branches having a generally short zigzag internodal growth configuration;
(c) the propensity to form spines on at least some branches; and
(d) the formation of mature leaves that commonly possess severely curled leaflets.

The bushy plant has twisted branches which display an unusual "natural bonzai" appearance unlike other plants of the species. Such characteristics readily distinguish the new variety from the parent species. The dimensions of the leaflets and compound leaves generally correspond to those of the parent species if one disregards the distinctive curled nature of the mature leaflets of the new variety.

The oldest available plant of the new variety is now approximately nine years of age and has a height of approximately three meters and a width of approximately two meters. A five-year old plant of the new variety under normal growth conditions commonly has a height of approximately one meter.

The new variety is particularly well suited for growing as a distinctive decorative shrub. It can be grown to advantage in containers or tubs that are present on balconies and terraces. It also can serve as attractive ornamentation in the urban landscape or in the garden when combined with other ornamentals.

The new variety has been found to well undergo asexual propagation by grafting on *Robinia pseudoacacia* rootstock. More specifically, such grafting when carried out at Kumeu, near Auckland, New Zealand and at St. Barthélémy d'Anjou, France has demonstrated that the unique combination of characteristics of the new variety is well established and is well transmitted to successive generations following asexual propagation. The resulting plants consistently exhibit the same combination of characteristics as the parent plants. The new variety is susceptible to common herbicides. No indexing for virus infection has been carried out to date.

The new variety has been named the 'Lace Lady' variety, and is being marketed under the TWISTY BABY trademark.

BRIEF DESCRIPTION OF THE PHOTOGRAPH

The accompanying photograph shows as nearly true as it is reasonably possible to make the same in a color illustration of this character typical specimens of plant parts of the new variety. The plants were grown in containers above the ground at St. Barthélémy d'Anjou, France. A centimeter scale in 5 cm. increments is present at the bottom of the photograph for use in estimating the dimensions of the illustrated plant parts.

FIG. 1—illustrates a specimen of a mature branch in which a typical twisted configuration is apparent;

FIG. 2—illustrates a pair of young branches having a typical zigzag configuration with short internodes, and wherein the small spines which sometimes ase observed are visible on the left branch;

FIG. 3—illustrates a typical young compound leaf (upper surface) wherein no substantial curling of the leaves has yet occurred;

FIG. 4—illustrates a typical young compound leaf (under surface) wherein no substantial curling of the leaves has yet occurred;

FIG. 5—illustrates clusters of older compound leaves while attached to a twisted branch wherein the characteristic substantial curling of the leaves is visible; and FIG. 6—illustrates clusters of young compound leaves while attached to a young branch wherein no substantial curling of the leaves has yet occurred. FIG. 7—illustrates the overall bushy shrub growth habit of a typical five year-old specimen of the new variety. Unlike the others, this photograph was prepared during April 1995, at Angers, France.

DETAILED DESCRIPTION

The following description of the new variety was prepared during the observation of plants of the new variety growing above the ground in containers at St. Barthélémy d'Anjou, France, and at Kumeu, near Auckland, New Zealand.

Classification:

*Botanical.*—*Robinia pseudoacacia* cv. 'Lace Lady'.

Foliage:

*Type.*—Pinnate, deciduous, light green as illustrated, with opposite leaflets.

Leaflets:

*Shape.*—Ovoid, rounded to retuse at apex, and rounded at the base.

*Length.*—Commonly approximately 23 mm.

*Width.*—Commonly approximately 20 mm.

*Young leaflets.*—Upper surface: Weak pubescence. Under surface: Weak pubescence. Configuration: Not much twisting of the young leaflets generally is observed.

*Mature leaflets.*—Upper surface: Weak pubescence. Under surface: Weak pubescence. Configuration: Generally curled and twisted as illustrated.

*Shedding.*—The leaflets of the new variety are shed at approximately the same time as those of the species.

Branches:

*New growth.*—Color: Dark green brown.

Figures 1, 2, 3, 4, 5, 6:
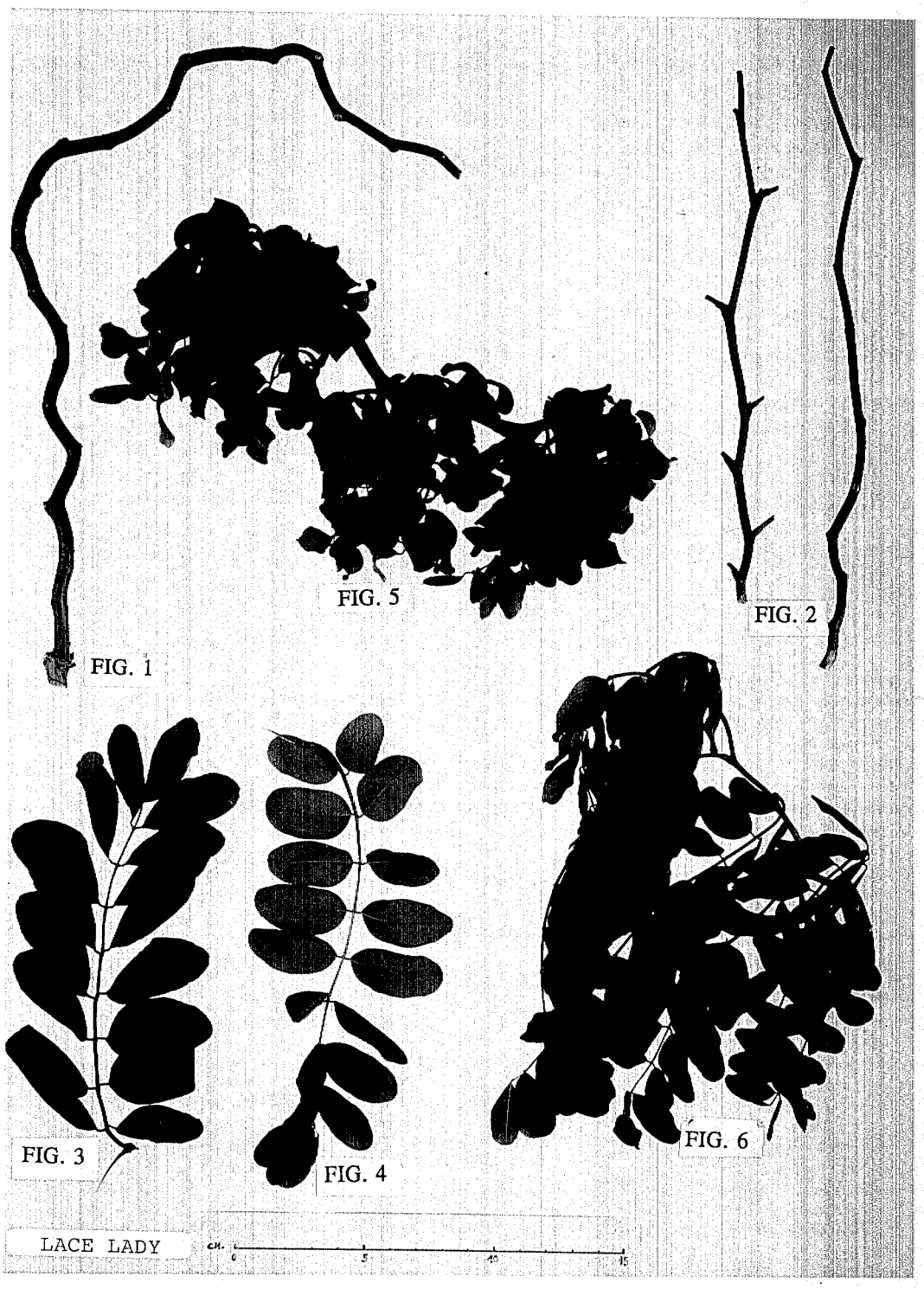
Figure 7:
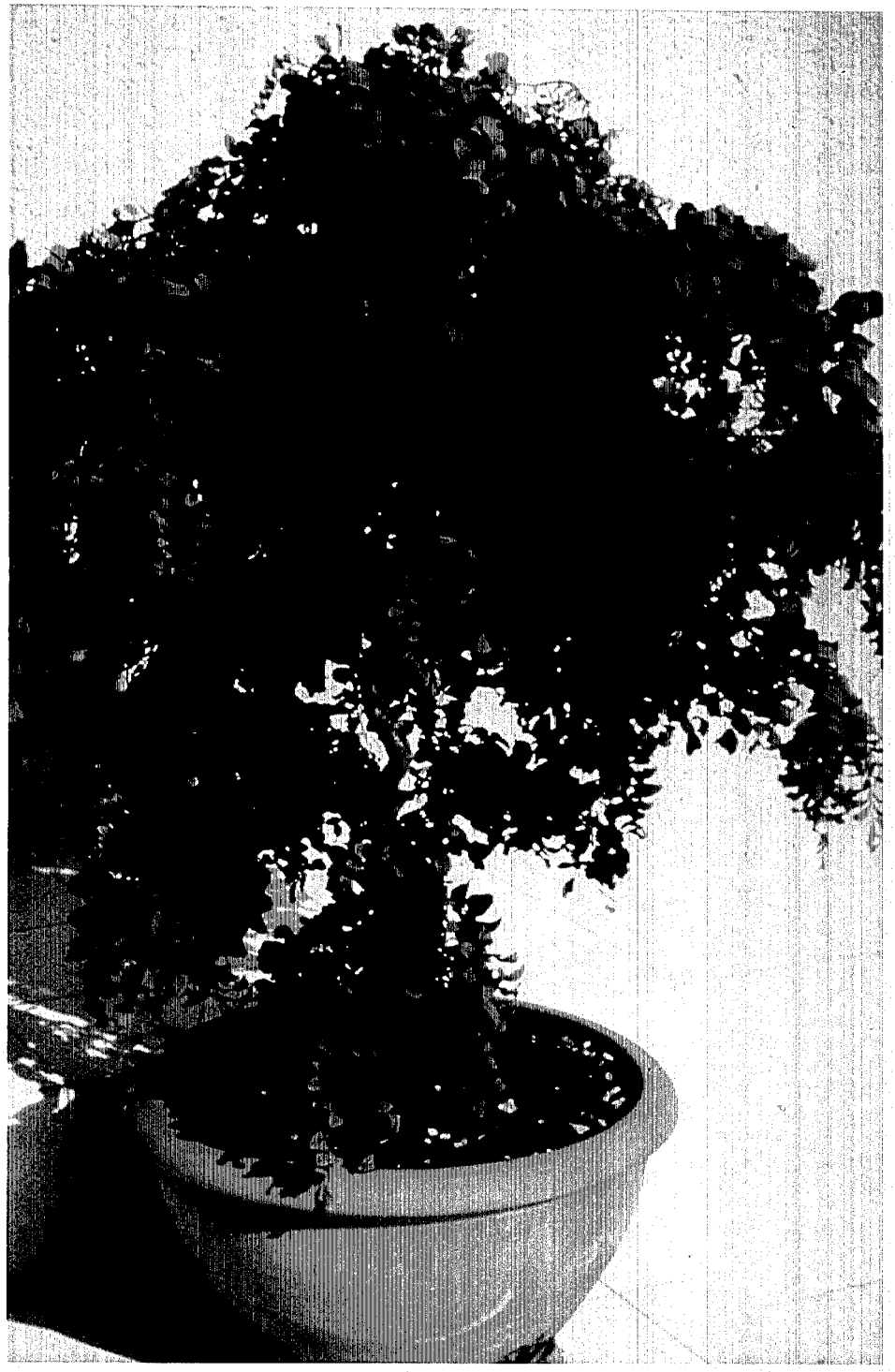

*Mature wood.*—General appearance: The surface generally is furrowed, commonly the branches are twisted, particularly the smaller branches exhibit a zigzag growth habit between nodes, and small spines sometimes are present particularly on younger branches. The angles between internodes commonly are approximately 130 degrees when the branches are young (as illustrated in FIG. 2). The main scaffold branches commonly are disposed at an angle of approximately 60 degrees with respect to the trunk. Color: Grey.

Inflorescence: White compact flowers that are typical of the species rarely are formed. No determination has been made to date of whether the flowers are fertile. Usually no flowers are observed. When flowers are formed they commonly are of substantially the same size and appearance as those of the parent species. No seed pods have been observed on the new variety to date.

Growth habit: A distinctive bushy shrub growth habit with zigzag young branches and curled mature leaves is exhibited. When both hot and wet growing conditions are encountered the internode lengths tend to be longer. There commonly is considerable variation in the internode lengths depending upon the growing conditions. The bushy new variety can be characterized as being non-weeping and commonly exhibits no distinct central leader. The crown of the new variety commonly is less than dense and the branches commonly exhibit a strength comparable to that of the parent species. The newly formed zig-zag branches tend to straighten somewhat with age.

I claim:

1. A new and distinct variety of *Robinia pseudoacacia* plant, substantially as illustrated and described, which exhibits:

(a) a bushy shrub shrub growth habit, (b) the formation of branches having a generally short zigzag internodal growth configuration, (c) the propensity to form spines on at least some branches, and (d) the formation of mature leaves that commonly possess severely curled leaflets.

* * * * *

LACE LADY
CM.
0
5
10
15